United States Patent
Traver et al.

Patent Number: 4,618,689
Date of Patent: Oct. 21, 1986

[54] NOVEL AMINOFUNCTIONAL SILICONE COMPOSITIONS

[75] Inventors: Frank J. Traver, Troy; Edward T. Simoneau, Greenwich, both of N.Y.

[73] Assignee: General Electric Company, Waterford, N.Y.

[21] Appl. No.: 756,481

[22] Filed: Jul. 18, 1985

[51] Int. Cl.$^4$ ............................................. C07F 7/10
[52] U.S. Cl. .................................. 556/425; 556/413; 556/415
[58] Field of Search ................. 556/413, 425, 415

[56] References Cited

U.S. PATENT DOCUMENTS

| | | | |
|---|---|---|---|
| 2,947,771 | 8/1960 | Bailey | 556/425 |
| 3,033,815 | 5/1962 | Pike et al. | 556/413 X |
| 3,203,969 | 8/1965 | Pines et al. | 556/425 |
| 4,045,460 | 8/1977 | Kleinstück | 556/413 |
| 4,152,346 | 5/1979 | Seiler et al. | 556/425 X |
| 4,526,996 | 7/1985 | Kilgour et al. | 556/413 |

*Primary Examiner*—Paul F. Shaver
*Attorney, Agent, or Firm*—Gary L. Loser

[57] ABSTRACT

A composition having the general formula

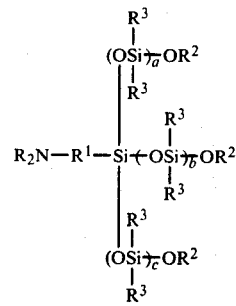

wherein each R is independently selected from hydrogen, substituted and unsubstituted organic radicals, and radicals of the formula —R$^1$NR$_2$ where R is as previously defined; R$^1$ is a divalent organic radical; each R$^2$ is independently selected from substituted and unsubstituted alkyl radicals having at least 12 carbon atoms; each R$^3$ is an independently selected organic radical having from 1 to 13 carbon atoms; and a, b, and c are, independently, 0 or a positive integer.

19 Claims, No Drawings

NOVEL AMINOFUNCTIONAL SILICONE COMPOSITIONS

BACKGROUND OF THE INVENTION

The present invention relates to novel higher alkoxy aminosilanes and aminosiloxanes. More particularly, the present invention relates to silicone compositions having the general formula

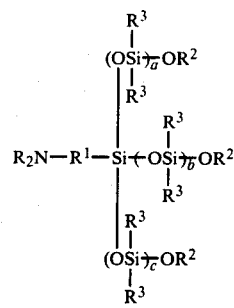

where each R is independently selected from hydrogen, substituted and unsubstituted organic radicals, and radicals of the formula —$R^1NR_2$ where R is as previously defined; $R^1$ is a divalent organic radical; each $R^2$ is independently selected from substituted and unsubstituted alkyl radicals having at least 12 carbon atoms; each $R^3$ is an independently selected organic radical having from 1 to 13 carbon atoms; and a, b, and c are, independently, zero or a positive integer.

Various aminosilanes and aminosiloxanes are known in the art as lubricants, crosslinking agents, or as polymers useful in preparing room temperature vulcanizable (RTV) compositions.

Eynon et al., U.S. Pat. No. 2,947,772, discloses silanes of the formula $$R\ Si(OR')_3$$

and siloxanes of the formula $$[R(R'O)_2Si]_2O$$

in which R is an alkyl group of from 8 to 20 carbon atoms and R' is a branched chain alkyl group of 4 to 20 carbon atoms having branching at the carbon atom beta to the oxygen.

Speier, U.S. Pat. No. 2,971,864, discloses silanes of the formula $$(RO)_3SiR'Z_n$$

wherein R is an alkyl radical of less than 4 carbon atoms, R' is an aliphatic hydrocarbon radical, n is an integer of at least 1, and Z is a monovalent radical attached to R' through a carbon-nitrogen bond, and is composed of hydrogen and carbon atoms and at least two amine groups.

Pepe et al., U.S. Pat. No. 3,054,818, provides silicon-nitrogen compounds of the formula

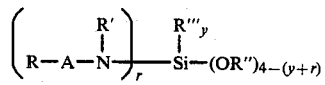

where A is a divalent aromatic hydrocarbon radical, R is hydrogen, fluorine or a monovalent organic radical free of reactive halogen or reactive hydrogen, R" is a monovalent hydrocarbon radical, R''' is a monovalent hydrocarbon radical, y has a value of 0 to 3, inclusive, r equals 1 or 2, and R' is hydrogen, an alkyl, aryl, aralkyl, cycloalkyl or an

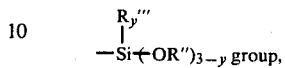

group, where R" and R''' are as previously defined.

Speier, U.S. Pat. No. 3,504,998, teaches the use of silanes having the formula $$R''_x(Z_nR')Si(OR)_{3-x}$$

where x is an integer equal to 0 or 1, each R is an alkyl radical of less than four carbon atoms, R' is an aliphatic hydrocarbon radical, Z is a monovalent radical attached to R' by a carbon-nitrogen bond and is composed of carbon, nitrogen and hydrogen atoms and contains at least two amine groups, in a process for dyeing textiles.

Golitz, U.S. Pat. No. 3,621,047, discloses novel crosslinking agents having the formula $$[(RO)_3Si\text{—}CH(R')\text{—}]\text{—}_nNQ_{3-n}$$

wherein n equals 2 or 3, R is an alkyl radical having 1 to 4 carbon atoms, R' is a hydrogen atom, an alkyl radical with 1 to 6 carbon atoms, a cyclohexyl radical or a phenyl radical, and Q is an alkyl or alkenyl radical with 2 to 4 carbon atoms, an aralkyl radical with 7 to 10 carbon atoms, a dimethylaminoalkyl radical with 2 to 4 carbon atoms, or a methoxy, ethoxy, ethyl or propyl radical.

Seiler, U.S. Pat. No. 3,864,373, relates to alkoxysilylethylamino compounds of the formula

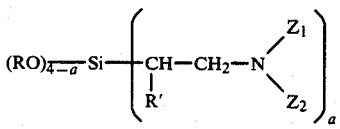

where a is 1, 2 or 3, R is a lower substituted or unsubstituted alkyl radical, R' represents a substituted or unsubstituted alkyl radical, and $Z_1$, and $Z_2$ each represent hydrogen or alkyl, alkenyl, cycloalkyl or phenyl radicals.

Kleinstuck, U.S. Pat. No. 4,045,460, provides a method for making an aminoalkylsilane of the formula $$(RO)_{3-n}R_n{}^1SiR^2NH_2$$

wherein n is an integer from 0 to 3, R is an alkyl or alkoxyalkyl radical with 1 to 8 carbon atoms in each alkyl radical, or an aryl radical with up to 10 carbon atoms, $R^1$ is an alkyl radical with up to 8 carbon atoms or an aryl radical with up to 10 carbon atoms, and $R^2$ is a divalent hydrocarbon radical with 2 to 10 carbon atoms.

Kappler et al., U.S. Pat. No. 4,234,503, discloses a process for preparing gamma-aminopropylakoxysilanes of the formula

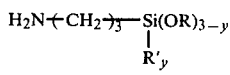

where R is an alkyl radical of 1 to 4 carbon atoms, R' is methyl or phenyl, and y equals 0, 1 or 2.

Wheeler, U.S. Pat. No. 3,133,111, provides an improved method for the transesterification of an alkoxy-containing organosilicon compound with a hydroxy-containing organic compound which comprises reacting an organosilicon compound containing at least one alkoxy group attached to silicon and a hydroxy-containing organic compound selected from the class consisting of monohydric aliphatic hydrocarbon alcohols, glycols, phenols and hydroxy-containing polyoxyalkylene ethers in contact with an organic acid selected from the class consisting of aliphatic acids, chlorinated aliphatic acids and perfluoroaliphatic acids and a base compound selected from the class consisting of alkali metal hydroxides and organic salts thereof, ammonium hydroxide and the organic salts thereof, and nitrogen-containing organic bases containing a trivalent nitrogen atom and the organic salts thereof.

None of these references, however, disclose or suggest silicone compositions of formula I hereinabove which has been found to be especially useful in wax formulations.

SUMMARY OF THE INVENTION

It is an object of the present invention to provide novel higher alkoxy aminosilanes and aminosiloxanes which are especially useful as waxes.

It is another object of the present invention to provide methods for making the novel higher alkoxy aminosilanes and aminosiloxanes of the present invention.

In accordance with the objects of the present invention there are provided novel silicon compositions having the general formula

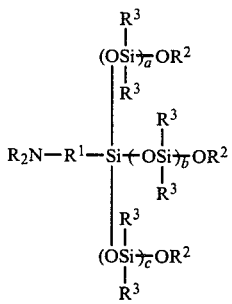

wherein each R is independently selected from hydrogen, substituted and unsubstituted organic radicals, and radicals of the formula —R$^1$NR$_2$, where R is as previously defined; R$^1$ is a divalent organic radical; each R$^2$ is independently selected from substituted and unsubstituted alkyl radicals having at least 12 carbon atoms; each R$^3$ is an independently selected organic radical having from 1 to 13 carbon atoms; and a, b and c are, independently, zero or a positive integer.

DESCRIPTION OF THE INVENTION

The present invention provides novel higher alkoxy aminosilanes and aminosiloxanes having the general formula

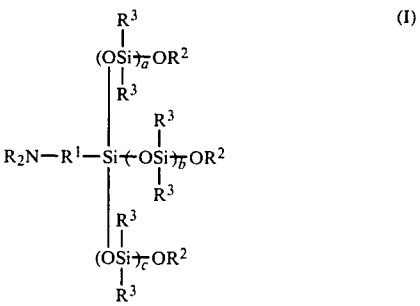

wherein each R is independently selected from hydrogen, substituted and unsubstituted organic radicals, and radicals of the formula —R$^1$NR$_2$, where R is as previously defined; R$^1$ is a divalent organic radical; each R$^2$ is independently selected from substituted and unsubstituted alkyl radicals having at least 12 carbon atoms; each R$^3$ is an independently selected organic radical having from 1 to 13 carbon atoms; and a, b and c are, independently, 0 or a positive integer.

It will be apparent to those skilled in the art that silanes are obtained when a, b, and c are all equal to zero, and that siloxanes are obtained when at least one of a, b and c is a positive integer. Preferably, a, b and c have values ranging from 0 to 10 and, more preferably, from 0 to 5, since too many diorganosiloxy units will cause the resultant composition to be oily rather than a solid wax. Of course, suitable values for a, b and c can readily be ascertained by the artisan without undue experimentation.

R radicals suitable for practicing the present invention include hydrogen; substituted and unsubstituted organic radicals which preferably are substituted and unsubstituted hydrocarbon radicals such as alkyl radicals, for example, methyl, ethyl, propyl, butyl, and the like, aryl radicals, for example, phenyl, tolyl, xylyl, and the like, alkaryl, for example, β-phenylethyl and the like, alkaryl, for example, benzyl and the like, substituted radicals of any of the foregoing, for example, chloroethyl, 3,3,3-trifluoropropyl, β-cyanoethyl, and the like; and —R$^1$NR$_2$ radicals where R$^1$ is a divalent organic radical such as a hydrocarbon and R is as previously defined, for example, aminoethyl, aminopropyl and the like.

R$^1$ is a divalent organic radical which preferably is a substituted or unsubstituted hydrocarbon radical such as alkylene, for example, methylene, ethylene, propylene, butylene, and the like; arylene, for example, phenylene, naphthylene, and the like; or a halogen substituted radical of any of the foregoing.

Examples of suitable R$_2$NR$^1$ moieties bonded to silicon in formula I thus includes

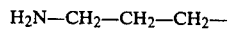

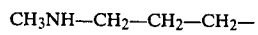

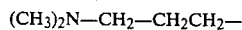

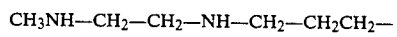

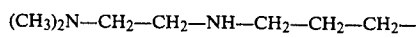

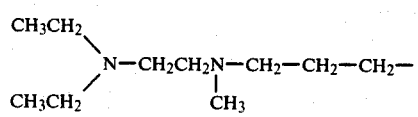

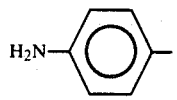

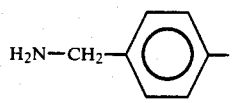

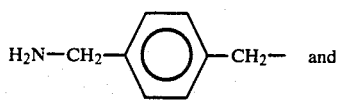

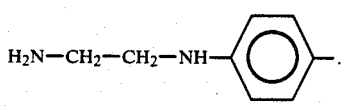

The foregoing list is only for purposes of illustration and is not intended to be all inclusive. Other variations within the scope of the appended claims will be obvious to those of ordinary skill in the art.

$R^2$ radicals employed in the practice of the present invention can be any substituted or unsubstituted alkyl radicals having at least 12 carbon atoms and, preferably, from 14 to about 30 carbon atoms. Most preferably, $R^2$ is an unsubstituted linear hydrocarbon radical having from 14 to 25 carbon atoms, for example, dodecyl, pentadecyl, octadecyl, eicosyl, and the like. Other suitable $R^2$ radicals can readily be ascertained without undue experimentation.

$R^3$ can be any substituted or unsubstituted organic radical having from 1 to 13 carbon atoms and preferably is a substituted or unsubstituted hydrocarbon, such as methyl, ethyl, propyl, butyl, chloroethyl, 3,3,3-trifluoropropyl, vinyl, phenyl, cyanoethyl, or mixtures thereof. Most preferably $R^3$ is methyl or a mixture of a major amount of methyl and a minor amount of phenyl, cyanoethyl, trifluoropropyl, vinyl or mixture thereof.

Preferred embodiments of the compositions of the present invention as well as methods for making such compositions are described in detail in the examples which follow. All parts are by weight unless otherwise noted.

EXAMPLES

Example 1

Aminoethylaminopropyltrioctadecyloxysilane was prepared by adding to a one liter 3-neck round bottom flask equipped with mechanical stirrer, heating mantle, thermometer, thermal controller, take-off head and condensor, 300 grams of stearyl alcohol (1-octadecanol), 81.4 grams of aminoethylainopropyl-trimethoxysilane, and 0.6 grams of potassium hydroxide pellets. The mixture was heated to 180° C. and held for three hours. While heating to 180° C. and during the cook, methanol was removed from the reaction vessel in the take-off head reservoir. Nearly 1.1 mols of methanol was removed.

IR scans of the material indicated a reduction of the OH peak. After the transalkoxylation reaction was completed, the KOH catalyst was neutralized with 1.1 gram trischloroethyl phosphite at 160°-180° C. The product was then stripped to 260° C. at 20 mm pressure to remove any unreacted stearyl alcohol and filtered throguh Celite #545. The resultant product melted at 42°-44° C.

Example 2

N-trioctadecyloxysilylpropyl-N,N,N-trimethylammonium chloride was prepared by adding to a one liter 3-neck vessel equipped as in Example 1, 135 grams of stearyl alcohol and 86 grams N-trimethoxysilylpropyl-N,N,N-trimethylammonium chloride in methanol (50% active). The pot was heated to 80° C. to remove free methanol and melt the stearyl alcohol.

Once the free alcohol was removed, 0.4 gram of trifluoroacetic acid was added and the material heated to 150° C. The ingredients were cooked until the expected methanol was removed and the hydroxyl peak on the IR scan was reduced.

After the reaction was complete, the catalyst was neutralized with sodium bicarbonate. Once neutral, the product was stripped to 130° C. at 30 mm, then dissolved in a mixture of hexane, toluene and methanol, filtered through Celite #545 and Fuller's Earth, and stripped free of solvent.

Example 3

Tris (dimethyloctadecyloxysilyl) aminoethylaminopropyl sesquisiloxane was prepared by adding to a vessel equipped as in Example 1, 13 grams (5% active) of potassium silanolate solution in dimethylpolysiloxane fluid having trimethylsiloxy and silanol terminal groups, and 61 grams of octamethylcyclotetrasiloxane. The vessel was heated to 180° C. to equilibrate. After 30 minutes at 180° C., the vessel was cooled to 155° C. and 74 grams of aminoethylaminopropyltrimethoxysilane added. The reaction mixture was equilibrated for an additional hour, at which time the vessel was cooled to 90° C. and 270 grams of stearyl alcohol added. The material was then heated to 180° C. to allow transalkoxylation and the resultant methanol was removed. When the transalkoxylation was complete, the catalyst was neutralized at 180° C. with trischloroethyl phosphite. The product was stripped to 260° C. at 20 mm pressure and then filtered through Celite #545. The product melted at 28°-34° C.

Example 4

To a vessel equipped as in Example 1, there was added 74 grams of aminoethylaminopropyltrimethoxysilane, 24 grams of octamethylcyclotetrasiloxane, and 13 grams potassium silanolate solution as in Example 3. The silane/siloxane mixture was blended and then 270 grams of stearyl alcohol was added. The vessel was then heated to 180° C. for three hours to equilibrate and transalkoxylate. About one mol of methanol was removed during the heat cycle. Thereafter, the catalyst was neutralized with trischloroethyl phosphite, the product stripped to 260° C. at 20 mm pressure, and filtered through Celite #545. The product melted at 36°-38° C.

Example 5

To a vessel equipped as in Example 1, there was added 17.9 grams of aminopropyltrimethoxysilane, 66.6 grams of aminoethylaminopropyltrimethoxysilane, 0.60 grams KOH, and 324 grams of stearyl alcohol. The reaction mixture was then processed as in Example 1. The product melted at 39°–41° C.

All of the foregoing compositions are suitable for textile finishes, cosmetic bases, polishes, hair care products, and paper products.

We claim:

1. A composition having the general formula

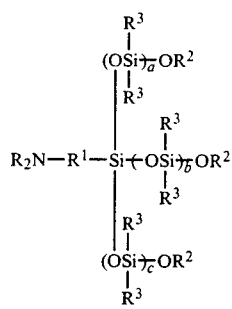

wherein each R is independently selected from hydrogen, substituted and unsubstituted organic radicals, and radicals of the formula —$R^1NR_2$, where R is as previously defined; $R^1$ is a divalent organic radical; each $R^2$ is independently selected from substituted and unsubstituted alkyl radicals having at least 14 carbon atoms; each $R^3$ is an independently selected organic radical having from 1 to 13 carbon atoms; and a, b and c are, independently, 0 or a positive integer.

2. A composition as in claim 1, wherein a, b and c have values ranging from 0 to 10, inclusive.

3. A composition as in claim 1, wherein a, b and c have values ranging from 0 to 5, inclusive.

4. A composition as in claim 1, wherein a, b and c are all equal to zero.

5. A composition having the general formula

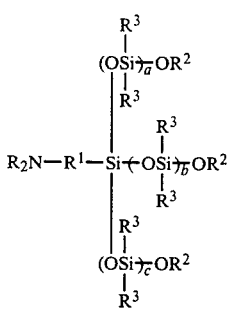

wherein each R is independently selected from hydrogen, substituted and unsubstituted organic radicals, and radicals of the formula —$R^1NR_2$, wherein R is as previously defined, with the proviso that at least one R is an —$R^1NR_2$ radical, where $R^1$ is a divalent organic radical, each $R^2$ is independently selected from substituted and unsubstituted alkyl radicals having at least 12 carbon atoms; each $R^3$ is an independently selected organic radical having from 1 to 13 carbon atoms; and a, b and c are, independently, 0 or a positive integer.

6. A composition as in claim 5 wherein the $R_2N$—$R^1$ radical bonded to silicon is aminoethylaminopropyl.

7. A composition as in claim 1, wherein $R^2$ has from 14 to about 30 carbon atoms.

8. A composition as in claim 1, wherein $R^2$ is an unsubstituted linear hydrocarbon radical having from 14 to about 25 carbon atoms.

9. A composition as in claim 8 wherein $R^2$ has at least 18 carbon atoms.

10. A composition as in claim 7, wherein $R^3$ is methyl or a mixture of a major amount of methyl and a minor amount of phenyl, cyanoethyl, trifluoropropyl, vinyl or mixture thereof.

11. A composition having the general formula

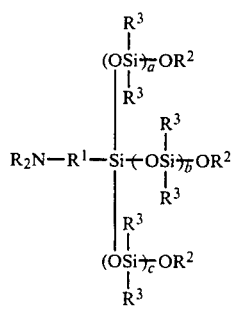

wherein each R is independently selected from hydrogen, substituted and unsubstituted organic radicals, and radicals of the formula —$R^1NR_2$, where R is as previously defined; $R^1$ is a divalent organic radical; each $R^2$ is independently selected from substituted and unsubstituted alkyl radicals having at least 12 carbon atoms; each $R^3$ is an independently selected organic radical having from 1 to 13 carbon atoms, and one or more of a, b and c is a positive integer.

12. A composition as in claim 11, wherein one or more of a, b and c has a value ranging from 1 to 10, inclusive.

13. A composition as in claim 11, wherein one or more of a, b and c has a value ranging from 1 to 5.

14. A composition as in claim 11, wherein at least one R is an —$R^1NR_2$ radical, where $R^1$ is a divalent organic radical and R is independently selected from hydrogen atoms and substituted and unsubstituted organic radicals.

15. A composition as in claim 14, wherein the —$R^1NR_2$ radical bonded to silicon is aminoethylaminopropyl.

16. A composition as in claim 11, wherein $R^2$ has from 14 to about 30 carbon atoms.

17. A composition as in claim 11, wherein $R^2$ is an unsubstituted linear hydrocarbon radical having from 14 to about 25 carbon atoms.

18. A composition as in claim 17, wherein $R^2$ has at least 18 carbon atoms.

19. A composition as in claim 16, wherein $R^3$ is methyl or a mixture of a major amount of methyl and a minor amount of phenyl, cyanoethyl, trifluoropropyl, vinyl or mixture thereof.

* * * * *